United States Patent [19]

Moser

[11] Patent Number: Plant 6,941

[45] Date of Patent: Jul. 25, 1989

[54] HIBISCUS PLANT NAMED MAUI SUNSET

[75] Inventor: Frank C. Moser, Alva, Fla.

[73] Assignee: Yoder Brothers, Inc., Barberton, Ohio

[21] Appl. No.: 160,013

[22] Filed: Feb. 24, 1988

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Hibiscus plant named Maui Sunset particularly characterized by its bright orange flower color, semi-double flower form, excellent pot habit, resistance to Bacterial Leaf Spot, good flower production, ease of rooting cuttings, flower life of a single day, medium sized leaves with a slightly serrated edge, and durability as a landscape subject.

3 Drawing Sheets

The present invention comprises a new and distinct cultivar of Hibiscus, botanically known as *Hibiscus rosa-sinensis* L., and referred to by the cultivar name Maui Sunset. The new cultivar was previously identified as 86X04001, and is a product of a mutation induction program which had the objective of creating new hibiscus cultivars that would expand the color range of an existing cultivar while retaining all other traits.

Maui Sunset is a spontaneous mutation and was discovered and selected by Frank C. Moser on Feb. 15, 1986 as one flowering branch of a large landscape hibiscus tree planted around the main office of the Technical Business Group of Yoder Brothers, Inc., Alva, Fla. The parent cultivar is Anderson's Double Yellow Red.

The first asexual reproduction of Maui Sunset was accomplished when vegetative cuttings were taken from the initial plant selection on Jan. 5, 1987 in Fort Myers, Fla. from a plant grown outside in ground beds, by technicians working under formulations established and supervised by Frank C. Moser.

Horticultural examinations of controlled flowerings of successive generations of plants derived from cuttings taken from the original selection have shown that the unique combination of characteristics as herein disclosed for Maui Sunset are fixed and retained through successive generations of asexual reproduction.

Maui Sunset has not been observed under all possible environmental conditions. The phenotype may vary significantly with variation in environment such as temperature and light intensity.

The following observations, measurements and comparisons describe plants that were grown in Fort Myers, Fla. in a controlled greenhouse environment and following a commercial schedule.

The following traits have been repeatedly observed and are determined to be basic characteristics of Maui Sunset, which, in combination, distinguish this Hibiscus as a new and distinct cultivar:

1. Bright orange semi-double flower.
2. Excellent pot habit.
3. Resistance to Bacterial Leaf Spot.
4. Good flower production.
5. Ease of rooting cuttings.
6. Flower life is a single day.
7. Medium sized leaves with slightly serrated edge.
8. Durability as a landscape subject.

The accompanying photographic drawings show typical habit, flower and leaf characteristics of Maui Sunset, with colors being as nearly true as possible with illustrations of this type.

Sheet 1 is a color photograph of Maui Sunset grown as a commercially finished pot plant.

Sheet 2 is a color photograph illustrating the distinctive characteristics of the upper and lower surfaces of the flower.

Sheet 3 is a color photograph showing the variation in leaf shape that can characteristically be found on any one plant of Maui Sunset.

Of the commercial cultivars known to the inventor, the most similar in comparison to Maui Sunset is the parent cultivar Anderson's Double Yellow Red. All traits of Maui Sunset are similar to those of Anderson's Double Yellow Red except for flower color, which in Maui Sunset is bright orange shading to pink at the base of the petals, while Anderson's Double Yellow Red is bright red.

In the following description, color references are made to The Royal Horticultural Society Colour Chart. The color readings were taken from greenhouse grown plants on Oct. 15, 1987. All readings were taken in an office under cool white fluorescent lights, facing a west window between the hours of 10:00 a.m. and 2:00 p.m.

Classification:

*Botanical.*—*Hibiscus Rosa-sinensis* L. cv. Maui Sunset.

*Commercial.*—Greenhouse pot crop.

INFLORESCENCE

A. Flower (General):

*Size.*—Medium, 14 cm.

*Borne.*—In axils of leaves, 1 per node.

*Form.*—Semi-double.

*Life.*—1 day.

*Fragrance.*—None.

*Blooming habit.*—Continuously, year round.

B. Corolla (Petals):

*Texture.*—Smooth, veins slightly raised.

*Substance.*—Medium thick.

*Shape.*—Variable.

*Color (fully open).*—Upper surface: Veins — Orange 30A–32A. Interveinal — Orange 33C. Base of petals — Pink 52C. Lower surface: Peach 32D to 33D (right $\frac{2}{3}$); left $\frac{1}{3}$ is yellow 16D; base of petal is pink 52D.

C. Bud (1 day prior to opening):
*Size.*—6 cm in length.
*Shape.*—Ovate, rounded.

D. Calyx: Cup shaped, 5 pointed lobes, a single prominent midvein per lobe, membranous
*Length.*—4 cm.
*Color.*—Green 143A–143B.

E. Epicalyx: 6–8 pointed, narrow, sword-shaped bracts
*Length.*—2–2.5 cm.
*Color.*—Dark green 137B.

F. Peduncle:
*Length.*—3–5 cm.
*Strength.*—Medium.
*Aspect.*—Smooth.
*Color.*—Green 144B.

G. Reproductive organs:
(1) *Androecium* (*stamens*).—Anthers: Numerous. Filaments: Length 6 mm. Pollen: Medium, Color is yellow 15A. Staminal column: Length 7 cm, Color white, Upper 30% antheriferous. Lower 70% petaloid.
(2) *Gynoecium* (*pistil*).—Stigma: 5 in number, rounded, discoid, hairy. Color: Orange 33A. Style: Length 8.5 cm, Color white. Branches: 5 in number, color yellow 6D. Ovary: Cylindrical, elongate, rarely functional. Color green 145D.

PLANT CHARACTERISTICS

A. Foliage:
*Arrangement.*—Alternate.
*Shape.*—Juvenile: Entire. Mature: Entire, cordate, serrated edge. Color: Dark green 139A.
*Petiole.*—Length 3.5–6 cm, Aspect smooth. Color: Green 143B.
*Stipules.*—2 per node, Shape acicular (needle shaped). Color: Green 143B.

B. Stems: Aspect smooth, becoming woody with age.
C. Plant habit: Semi-compact.
D. Breaking action: Good.
E. Rooting: Good.
F. Growth regulator: Required.
G. Low light bud initiation: Fair.
H. Shipping tolerance: Good.
J. Landscape potential: Excellent.

I claim:

1. A new and distinct cultivar of *Hibiscus rosa-sinensis* named Maui Sunset, as illustrated and described, and parts thereof.

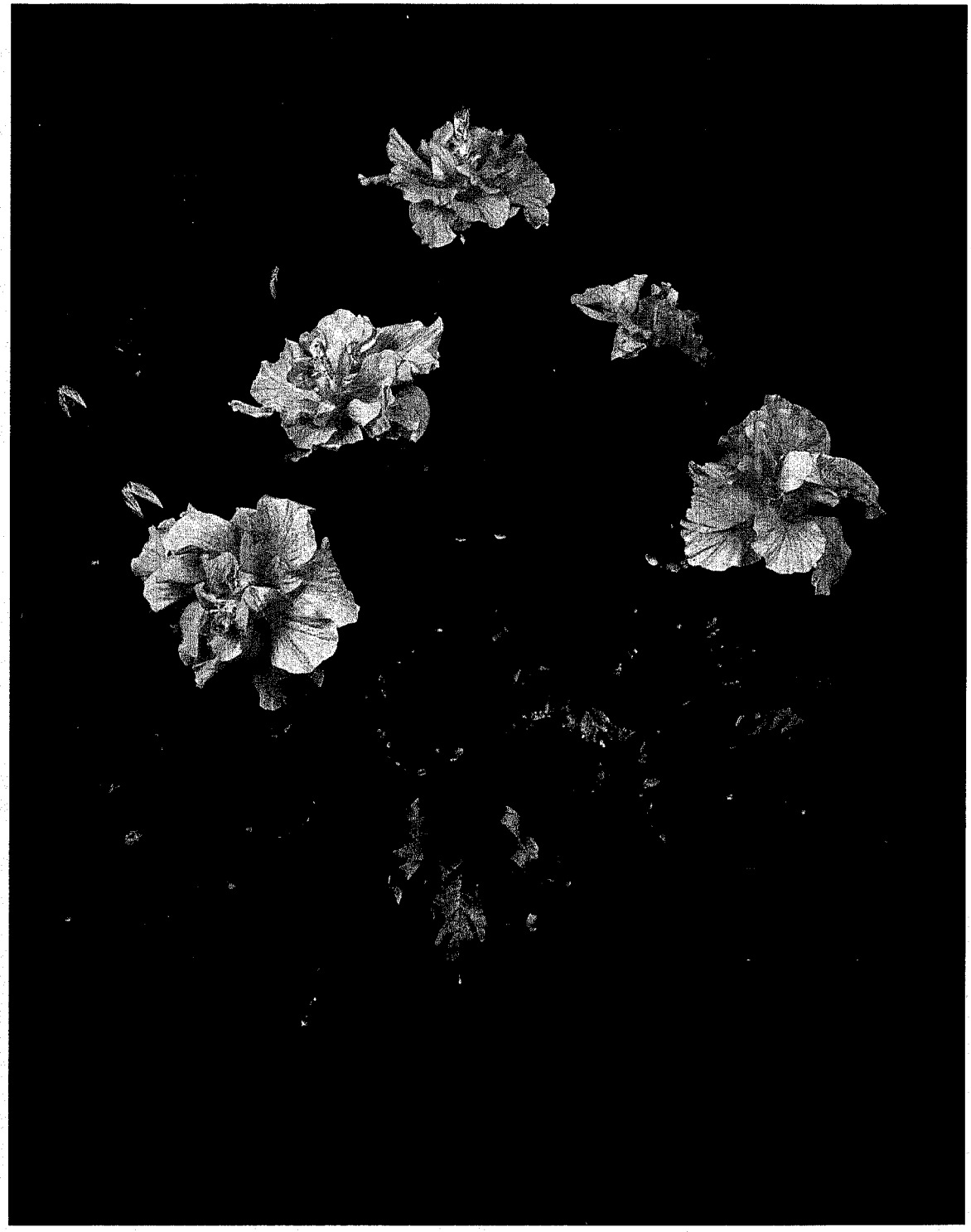

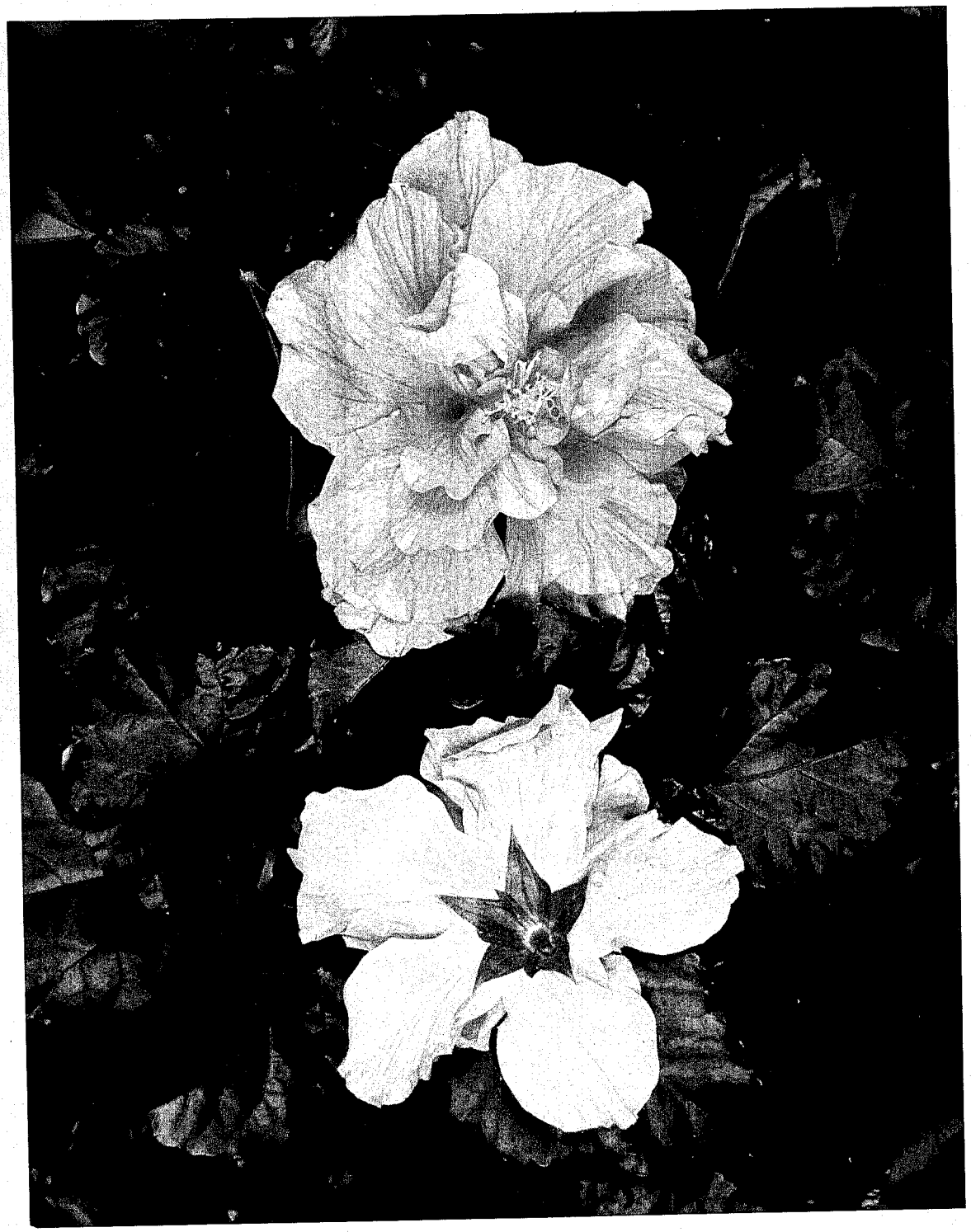

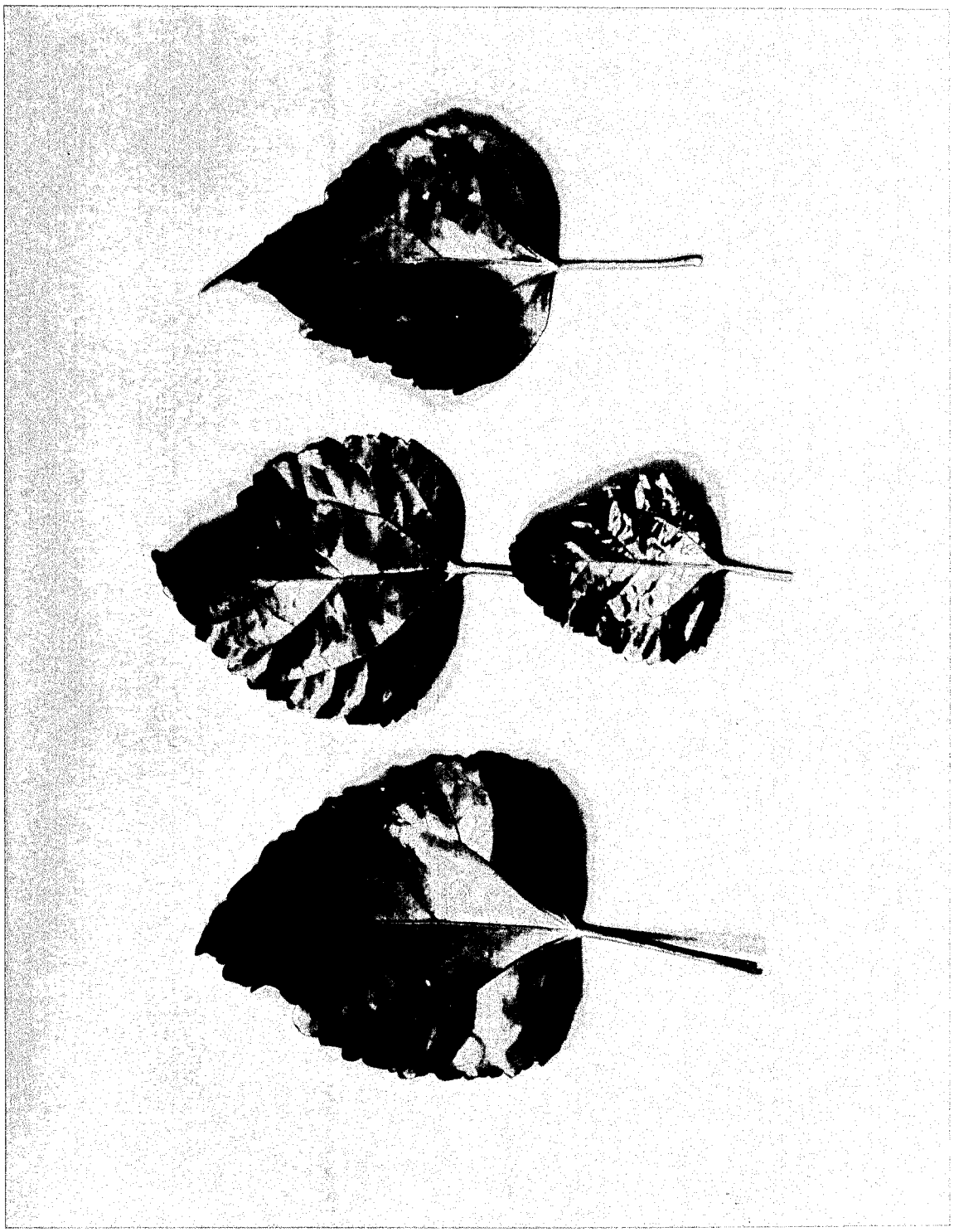

* * * * *